US007217506B2

(12) United States Patent
De Meyer et al.

(10) Patent No.: US 7,217,506 B2
(45) Date of Patent: May 15, 2007

(54) MUTATIONAL PROFILES IN HIV-1 PROTEASE CORRELATED WITH PHENOTYPIC PROTEASE INHIBITOR RESISTANCE

(75) Inventors: Sandra De Meyer, Beerse (BE); Hilde Azijn, Leuven (BE); Marie-Pierre T. M. M. G De Bethune, Everberg (BE)

(73) Assignee: Tibotec Pharmaceuticals, Ltd.

( * ) Notice: Subject to any disclaimer, the term of this patent is extended or adjusted under 35 U.S.C. 154(b) by 0 days.

(21) Appl. No.: 10/519,035

(22) PCT Filed: Jun. 30, 2003

(86) PCT No.: PCT/EP03/50277

§ 371 (c)(1),
(2), (4) Date: Dec. 22, 2004

(87) PCT Pub. No.: WO2004/003817

PCT Pub. Date: Jan. 8, 2004

(65) Prior Publication Data

US 2005/0233312 A1    Oct. 20, 2005

Related U.S. Application Data

(60) Provisional application No. 60/392,753, filed on Jul. 1, 2002.

(51) Int. Cl.
*C12Q 1/00* (2006.01)
*C12Q 1/70* (2006.01)
*C12Q 1/68* (2006.01)
(52) U.S. Cl. .................................... 435/4; 435/5; 435/6
(58) Field of Classification Search ............... 435/5, 435/4, 6
See application file for complete search history.

(56) References Cited

U.S. PATENT DOCUMENTS 327,742 A    10/1885    Uren

FOREIGN PATENT DOCUMENTS

| EP | 406985 A2 | 1/1991 |
|---|---|---|
| EP | 428000 A1 | 5/1991 |
| WO | 97/27332 A1 | 7/1997 |
| WO | 97/27480 A1 | 7/1997 |
| WO | WO 97/23719 A1 | 7/1997 |
| WO | 99/67428 A2 | 12/1999 |
| WO | 00/73511 A1 | 12/2000 |
| WO | 00/78994 A1 | 12/2000 |
| WO | 00/78996 A1 | 12/2000 |
| WO | WO 01/79540 A2 | 10/2001 |
| WO | 01/81624 A1 | 11/2001 |
| WO | 01/95230 A2 | 12/2001 |
| WO | 02/22076 A2 | 3/2002 |
| WO | 02/33402 A2 | 4/2002 |
| WO | 02/38792 A2 | 5/2002 |
| WO | 02/083657 A2 | 10/2002 |
| WO | 04/022523 A2 | 3/2004 |

OTHER PUBLICATIONS

Shafer et al. Human Immunodeficiency Virus Reverse Transcriptase and Protease Sequence Database, Jan. 1999, Nucleic Acids Research, vol. 27, No. 1, pp. 348-352.*
Craig, et al. HIV protease genotype and viral sensitivity to HIV protease inhibitors following saquinavir therapy 1998. AIDS vol. 12, pp. 1611-1618.*
Shafer, et al. Highly active antiretroviral therapy for the treatment of infection with human immunodeficiency virus type 1, 1999. Biomedicine & Pharmacotherapy vol. 53, pp. 73-86.*
Parikh, et al. Mutations in retroviral genes associated with drug resistance 2000. [online]. HIV Sequence Database [retrieved on Dec. 9, 2005]. Retrieved from the Internet: <URL://hiv-web.lanl.gov/content/hiv-db/REVIEWS/reviews.html>.*
Abstract: International Congress on Drug Therapy in HIV Infection, vol. 12,Supplement 4, AIDS.online.com.
Abstract: Comprehensive HIV Drug Resistance Monitoring Using Rapid, High-Throughput Phenotypic and Geotypic Assays with Correlative Data Analysis. Poster Abstracts, OP3.4.
Condra, Jon ., et al. Genetic Correlates of InVivo Viral Resistance to Idivavir,a HumanImmunodefieiency Virus Thpe 1 Protease Inhibitor. Journal of Virology, Dec. 1996, pp. 8270-8276.
Guidance for Industry. U.S. Department of Health and Human Services, Food and Drug Administration.
Eastman, P. Scott, et al. Nonisotopic Hybridization Asay for Determinatin of Relative Amounts of Genotypic Human Immunodeficiency Virus Tpe 1 Zidovudine Resistance, Journal of Clinical Microbiology, Oct. 1995, pp. 2777-2780.
Eriksson, Bertil F.H., et al. Phosphorylation of 3'-Azido-2',3'-Dideoxyuridine and Preferential Inhibition of Human and Simian Immunodeficiency Virus Reverse Transcriptases by its 5'-Triphosphate. Antimicrobial Agents ad Chemotherapy, Oct. 1989, pp. 1729-1734.
Fodor,Stephen P.A., et al. Multiplexed Biochemical Assays With Biological Chips. Nature, Aug. 5, 1993, vol. 364, pp. 555-556.
Harada, Shinji, et al. Infection of HTLV-III/LAV in HTLV-I-Carring Cells MT-2 andMT-4 andApplicationin a Plaque Assay. Department o Virology and Prasitology, Yamaguchi University, Japan, Aug. 9, 1985, p. 563-566.

(Continued)

Primary Examiner—Jeffrey S. Parkin
Assistant Examiner—Louise Humphrey
(74) Attorney, Agent, or Firm—Yunling Ren

(57) ABSTRACT

The present invention is directed to the field of nucleic acid diagnostics and the identification of base variation in target nucleic acid sequences. More particularly, the present invention relates to the use of such genotypic characterization of a target population of HIV and the subsequent association, i.e., correlation, of this information to phenotypic interpretation in order to correlate virus mutational profiles with drug resistance. The invention also relates to methods of utilizing the mutational profiles of the invention in drug development, i.e., drug discovery, drug design, drug modification, and therapy, treatment design, clinical management and diagnostic analysis.

4 Claims, No Drawings

OTHER PUBLICATIONS

Hertogs, Kurt, et al. A Rapid Method for Simultaneous Detection of Pheotpic Resistance to Inhibitors of Protease and Reverse Transcriptase in Recombinant Human Immunodeficiency Virus Type 1 Isolates from Patients Treated with Antiretroviral Drugs. Antimicrobial Agents ad Chemotherapy, Feb. 1998, pp. 269-276.

Ibanex, Angela, et al. Human Immunodeficiency Virus Type 1 Population Bottleneck During Indinavir Theraphy Causes a Genetic Drift in the envquasispecies . . . Journal of General Virology, 2000, p. 85-95.

Konig, Herbert, et al. Azidothymidine Triphosphate Is an Inhibitor of Both Human Immunodeficiency Virus Type 1 Reverse Transcriptatse and DNA Polymerase Gamma. Antimicrobial Agents and Chemotherapy, Dec. 1989, pp. 2109-2114.

Larder, Brendan A., et al. Zidovudine Resistance Predicted by Direct Detection of Mutations in DNA from HIV-infected Lymphocytes. AIDS, 1991, 5:137-144.

Larder, Brendan A., et al. HIV with a Reduced Sensitivity to Zidovudine (AZT) Isolated During Prolonged Therapy. Reports, Mar. 31, 1980, pp. 1731-1734.

Lennerstrand, J., et al. A Method for Combined Immunoaffinity Purification and Assay of HIV-1 Reverse Transcriptase Activity Useful for Crude Samples. Analytical Biochemistry 235, 1996, pp. 141-152.

Matayoshi, Edmund D., et al. Novel Flurogenic Substrates for Assaying Retroviral Proteases by Resonance Energy Transfer. Science. vol. 247, pp. 954-958.

Miller, Veronica, et al. Patterns of Resistance and Cross-Resistance to Human Immunodeficiency Virus type 1 Reverse Transcriptase Inhibitors in Patents Treated with the Nonnucleoside Reverse Transcripatse Inhibitor Loviride. Antimicrobial Agents ad Chemotherapy, Dec. 1998, pp. 3123-3129.

Rusconi, Stefao, et al. Susceptibility to PNU-140690 (Tipranavir) of Human Immunodeficiency Virus Type 1 Isolates Derived from Patients with Multidrug Resistance to Other Protease Inhibitors. Antimicrobial Agents and Chemotherapy, May 2000, pp. 1328-1332.

Stuyver, Lieven, et al. Line Probe Assay for Rapid Detection of Drug-Selected Mutations in the Human Immunodeficiency Virus Type 1 Reverse Transcripatase Gene. Antimicrobial Agents and Chemotherapy, Feb. 1997, pp. 284-291.

Toth, Mihaly V., et al. A Simple, Continuous Flurometric Assay for HIV Protease. Int. J. Peptide Protein Res. 36, 1990, pp. 544-550.

Tyagi, Suresh C., et al. Continuous Assay of the Hydrolytic Activity of Human Immunodeficiency Virus-1 Protease. Analytical Biochemistry 200, pp. 143-145 (1992).

Tyagi, Sanjay, et al. Multicolor Molecular Beacons for Allele Discrimination. Nature Biotechnology, Jan. 1998, vol. 16, pp. 49-53.

Vasudevachari, M.B., et al. Emergence of Protease Inhibitor Resistance Mutations in Human Immunodeficiency Virus Type 1 Isolates from Patients and Rapid Screening Procedure for Their Detection. Antimicrobial Agents and Chemotherapy, Nov. 1996, pp. 2535-2541, vol. 40, No. 11.

Vergne, Lurence, et al. Genetic Diversity of Protease and Reverse Transcriptase Sequences in Non-Subtype-B Human Immunodeficiency Virus Type 1 Strains: Evidence of Many Minor Drug Resistance Mutations in Treatment-Naïve Patents. Journal of Clinical Microbiolog, Nov. 2000, p. 3919-3925, vol. 38, No. 11.

Wang, Gary T., et al. Design and Synthesis of New Fluorogenic HIV Protease Substrates Based on Resonance Energy Transfer. TetrahedronLetters, vol. 31, o. 45, pp. 6496-6496.

PCT Search Report dated Jan. 4, 2005, International Application No. PCT/EP 03/50280.

PCT Search Report dated Nov. 10, 2003,International Applcation No. PCT/EP 03/50277.

U.S. Appl. No. 10/519,436, filed Dec. 22, 2004.

U.S. Appl. No. 518,525, filed Dec. 22, 2004.

* cited by examiner

MUTATIONAL PROFILES IN HIV-1 PROTEASE CORRELATED WITH PHENOTYPIC PROTEASE INHIBITOR RESISTANCE

This application is the national stage of Application No. PCT/EP2003/050277, filed Jun. 30, 2003, which application claims priority from U.S. Application Ser. No. 60/392,753, filed Jul. 1, 2002.

The present invention is directed to the field of nucleic acid diagnostics and the identification of base variation in target nucleic acid sequences. The invention provides novel mutations or mutational profiles of HIV-1 protease gene correlated with a phenotype causing alterations in sensitivity to anti-HIV drugs. The present invention also relates to the use of genotypic characterization of a target population of HIV and the subsequent association, i.e. correlation, of this information to phenotypic interpretation in order to correlate virus mutational profiles with drug resistance. The invention further relates to methods of utilizing the mutational profiles of the invention in databases, drug development, i.e., drug design, and drug modification, therapy and treatment design and clinical management.

The development and standardization of plasma HIV-1 RNA quantification assays has led to the use of viral load measurements as a key therapy response monitoring tool. The goal of antiretroviral therapy is to reduce plasma viremia to below the limit of detection on a long-term basis. However, in a significant number of patients, maximal suppression of virus replication is not achieved and for those in whom this goal is reached, a significant number experience viral load rebound. Viral load data provide no information on the cause of the failure.

Therapy failure may be due to a number of factors, including insufficient antiviral activity of the regimen, individual variations in drug metabolism and pharmacodynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation which permits viral replication in the presence of an inhibitor sets the stage for selection of resistant variants.

Viral drug resistance can be defined as any change in the virus that improves replication in the presence of an inhibitor. HIV-1 drug resistance was first described in 1989 and involved patients that had been treated with zidovudine monotherapy (Larder, B. A., et al., Science 243, 1731-1734 (1989)). Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the antiretroviral compounds used. Resistance development has also been observed with the introduction of dual nucleoside reverse transcriptase inhibitors (NRTI) combination therapy as well as during the administering of the more potent non-nucleoside reverse transcriptase inhibitors (NNRTIs), protease inhibitors (PIs) and combinations thereof. Individual antiretroviral agents differ in the rate at which resistance develops: selection for resistant variants may occur within weeks of treatment or resistance may emerge after a longer treatment period.

Extensive genetic analysis of resistant viral isolates generated through in vivo or in vitro selection has revealed that resistance is generally caused by mutations at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled (See e.g. Schinazi, Int. Antiviral News. 6, 65 (2000)). Electronic listings with mutations are available at different web locations such as hiv-web.lanl.gov/content/index, www.hivb.stanford.edu, and www.hivresistanceweb.com.

A genetic mutation is normally written in reference to the wild type virus, i.e., K101N refers to replacement of a Lysine at codon 101 with a Asparagine (The Molecular Biology of the Cell, 1994, Garland Publishing, NY). However, the mutations of the invention do not depend on the wild-type example listed in order to be within the practice of the invention. For example, the mutation 101N, refers to an Asparagine at the 101 codon regardless of the whether there was a Lysine at 101 prior to mutation. Alternatively, it may be said that a particular amino acid occurs at a given position, wherein "position" is equivalent to "codon". Mutations can also be identified in nucleic acids such as RNA, DNA, mRNA.

The degree of susceptibility of a genetic variant to an antiretroviral compound is expressed herein relative to the wild-type virus (HIV IIIB/LAI reference sequence) as found, for example, in GenBank, the sequence of which is hereby incorporated by reference (K03455, gi 327742, M38432). An alteration in viral drug sensitivity is defined as a change in resistance or a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain can be expressed as a fold change in susceptibility, wherein the fold change is derived from the ratio of for instance the $EC_{50}$ values of a mutant viral strain compared to the wild type. In particular, the susceptibility of a viral strain or population may also be expressed as resistance of a viral strain, wherein the result is indicated as a fold increase in $EC_{50}$ as compared to wild type $EC_{50}$.

As antiretroviral drugs are administered for longer periods, mostly in combination with each other, and as new antiretrovirals are being developed and added to the present drugs, new resistance-correlated genetic variants are being identified. Of particular importance is that the combination of antiretroviral agents can influence resistance characteristics.

Once viral resistance has developed, salvage therapy options may be severely restricted due to cross-resistance within each drug class. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population.

A number of applications describe the occurrence of mutations in HIV and their correlation to the development of drug resistance (WO 00/73511; WO 02/33402; WO 02/22076; WO 00/78996). The instant invention adds to the art mutations in the protease gene and their correlation i.e. association to viral drug resistance.

DETAILED DESCRIPTION OF THE INVENTION

The knowledge that mutations at position 41 and 70 correlate with a fold change in resistance can be applied in certain useful methods. The present invention relates to methods for evaluating the effectiveness of a protease inhibitor, based on the presence of at least one mutation selected from 41S, 41T, 41I, 41K, 41G and 70E, in HIV protease. In particular, the present invention relates to methods for evaluating the effectiveness of a protease inhibitor, based on the presence of at least one mutation selected from 41T, 41I, 41K, 41G and 70E, in HIV protease. The presence of at least one of said mutations correlates to a fold change in susceptibility or resistance of an HIV viral strain towards at least one protease drug. The effectiveness of a protease inhibitor in the presence of at least one of said mutations may be determined using e.g. enzymatic, phenotypic and genotypic methods. The correlation between the mutational profiles in HIV protease and drug usage may be useful for clinical toxicological and forensic applications. A combined approach involving genotypic and phenotypic resistance testing to correlate mutations with resistance phenotypes may be used. More in particular, the present invention provides a correlation between at least one strain of HIV having at least one mutation in HIV protease selected from 41T and 70E and a fold change in resistance. In one aspect of the invention, the HIV protease mutations, 41T and 70E, are both present in a viral strain.

The effectiveness of a protease inhibitor as an antiviral therapy for a patient infected with at least one HIV strain comprising mutant protease may be determined using a method comprising: (i) collecting a sample from an HIV-infected patient; (ii) determining whether the sample comprises a HIV protease having at least one mutation selected from 41S, 41T, 41I, 41K, 41G, and 70E; and (iii) correlating the presence of said at least one mutation of step (ii) to a change in effectiveness of said protease inhibitor. In particular, the effectiveness of a protease inhibitor as an antiviral therapy for a patient infected with at least one HIV strain comprising mutant protease-may be determined using a method comprising: (i) collecting a sample from an HIV-infected patient; (ii) determining whether the sample comprises a HIV protease having at least one mutation selected from 41T, 41I, 41K, 41G, and 70E; and (iii) correlating the presence of said at least one mutation of step (ii) to a change in effectiveness of said protease inhibitor.

In general a change in effectiveness can be expressed as a fold change in resistance. The fold change may be determined using a cellular assay including a cytopathogenic assay or the Antivirogram® (WO 97/27480). Alternatively, the fold change in susceptibility may be derived from database analysis such as the VirtualPhenotype™ (WO 01/79540). A decrease in susceptibility vis-à-vis the wild type virus correlates to an increased viral drug resistance, and hence reduced effectiveness of said drug. To determine the viral drug susceptibility the activity of the mutant enzyme may be compared to the activity of a wild type enzyme. In phenotyping assays pseudotyped viruses may be used. The mutations present in HIV protease may be determined at the nucleic acid or amino acid level using sequencing or hybridization techniques. A report may be generated that shows the region of the patient virus that has been sequenced, including at least one mutation selected from 41S, 41T, 41I, 41K, 41G and 70E, in particular, including at least one mutation selected from 41T, 41I, 41K, 41G and 70E. The report may include antiretroviral drugs, drug(s) for which a known resistance-associated mutation has been identified and/or to what extent the observed mutations selected from at least 41S, 41T, 41I, 41K, 41G and 70E are indicative of resistance to said drugs. In particular, the report may include drug(s) for which a known resistance-associated mutation has been identified and/or to what extent the observed mutations selected from at least 41T, 41I, 41K, 41G and 70E are indicative of resistance to said drugs. HIV may be present in combinations of several strains. This may result in the presence of multiple mutations at a particular amino acid, including partial mutations. Partial mutations include the combination of the wild amino acid and a mutant amino acid at a particular position. Examples thereof include partial mutations at position 41 in HIV protease, including 41R/S, 41S/R, 41R/K, 41G/R, in particular 41R/K, 41G/R. The sample to be evaluated can be a bodily fluid including blood, serum, plasma, saliva, urine, or a tissue including gut tissues.

The fact that particular data correlate, indicates that a causal relationship exits between the data. Hence, a particular result renders a particular conclusion more likely than other conclusions.

A drug effective against mutant HIV protease may be identified by a method, comprising: (i) providing a nucleic acid comprising HIV protease comprising at least one mutation chosen from 41S, 41T, 41I, 41K, 41G and 70E; (ii) determining a phenotypic response to said drug for said HIV recombinant virus; and (iii) identifying a drug effective against mutant HIV based on the phenotypic response of step (ii). In particular, a drug effective against mutant HIV protease may be identified by a method, comprising: (i) providing a nucleic acid comprising HIV protease comprising at least one mutation chosen from 41T, 41I, 41K, 41G and 70E; (ii) determining a phenotypic response to said drug for said HIV recombinant virus; and (iii) identifying a drug effective against mutant HIV based on the phenotypic response of step (ii). The nucleic acid comprising HIV of step (i) may be recombined into a proviral nucleic acid deleted for said sequence to generate a recombinant HIV virus.

Identifying a drug is defined as making a selection of drugs clinically available based on the effectiveness of said drug. In addition to the selection of clinically available drugs, identifying also relates to the selection of clinical drug candidates. The phenotypic response may be determined using cellular assays such as the Antivirogram®. An effective drug against mutant HIV comprising at least one mutation in protease selected from 41T and 70E, is defined as a drug having a phenotypic response expressed, as e.g. a fold change in susceptibility lower than a defined cut-off that may be determined for a drug.

An other useful method for identifying a drug effective against mutant HIV protease comprising:
  (i) providing a HIV protease comprising at least one mutation chosen from 41S, 41T, 41I, 41K, 41G and 70E;
  (ii) determining the activity of said drug on said HIV protease;
  (iii) determining the activity of said drug on wild type HIV protease;
  (iv) determining the ratio of the activity determined in step (iii) over the activity determined in step (ii);

(v) identifying an effective drug against mutant HIV based on the ratio of step (iv).

In particular, a useful method for identifying a drug effective against mutant HIV protease comprising:

(i) providing a HIV protease comprising at least one mutation chosen from 41T, 41I, 41K, 41G and 70E;

(ii) determining the activity of said drug on said HIV protease;

(iii) determining the activity of said drug on wild type HIV protease;

(iv) determining the ratio of the activity determined in step (iii) over the activity determined in step (ii);

(v) identifying an effective drug against mutant HIV based on the ratio of step (iv).

A ratio lower than a defined cut-off value that can be specific for said drug is indicative that the drug is effective against mutant HIV (WO 02/33402).

The activity of said drug on said HIV protease, having at least one mutation selected from 41S, 41T, 41I, 41K, 41G and 70E, in particular 41T, 41I, 41K, 41G and 70E, can be determined in an enzymatic assay, wherein the mutant protease, is compared to the wild type enzyme by its enzymatic characteristics (e.g. Maximal velocity ($V_{max}$), Michaelis-Menten constant ($K_m$), catalytic constant ($k_{cat}$)). An activity means any output generated by the assay including fluorescence, fluorescence polarization, luminiscence, absorbance, radioactivity, resonance energy transfer mechanisms, magnetism. The use of fluorescent substrates to measure the HIV protease activity was described by e.g. Matayoshi et al. [Science 1990, 247, 954], Tyagi et al. [Anal. Biochem. 1992, 200(1), 143], Toth et al. [Int. J. Pept. Protein Res. 1990, 36(6), 544] and Wang et al. [Tetrahedron 1990, 31(45), 6493] and in several patent applications [see e.g. WO99/67417; EP428000, EP518557]. A suitable substrate for the enzymatic determination is R-E(EDANS)-S-Q-N-Y-P-I-V-Q-K(DABCYL)-R—OH (Science, 1989, 247, 954-958). Alternatively HPLC based methods may be used to determine the activity.

The response of a mutant HIV protease having at least one mutation selected from 41S, 41T, 41I, 41K, 41G and 70E, in particular 41T, 41I, 41K, 41G and 70E, may be expressed as viral fitness (WO 00/78994). This viral fitness can be defined as the ability of a viral strain to replicate in the presence or absence of a component, such as a protease inhibitor. This viral fitness is dependent on a combination of factors including viral factors which include mutations occurring in viral proteins, such as the mutations described herein, host factors which include immune responses, differential expression of membrane proteins and selective pressures which include the presence of antiviral agents such as protease inhibitors.

Interestingly, protease inhibitors that can be used in the present methods include Nelfinavir, Saquinavir, Indinavir, Amprenavir, Tipranavir, Lopinavir, Ritonavir, Palinavir, Atazanavir, Mozenavir, Fosamprenavir, compound 1 (Carbamic acid, [(1S,2R)-3-[[(4-aminophenyl)sulfonyl](2-methylpropyl)amino]-2-hydroxy-1-(phenylmethyl)propyl]-, (3R, 3aS,6aR)-hexahydrofuro[2,3-b]furan-3-yl ester, compound 1), and compound 2, which has been described as a HIV protease inhibitor in WO02/083657 and which can be prepared according to the procedures described therein. Compound 2 has the following chemical structure:

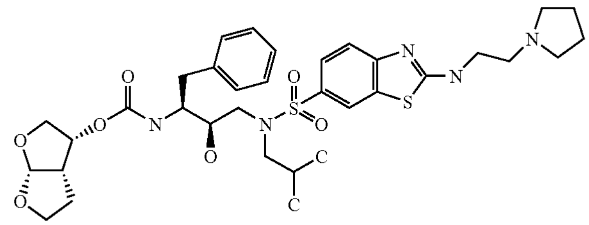

In an embodiment, the protease inhibitor is selected from Indinavir, Saquinavir, Lopinavir, Nelfinavir, compound 1, and compound 2. In particular, the protease inhibitor is selected from Indinavir, Saquinavir, Lopinavir and compound 1.

Conveniently, the methods of the present invention are performed using samples of an HIV-infected patient that has been treated with at least a protease inhibitor. More in particular, the patient contains mutant viruses bearing at least one additional mutation at position in the HIV protease selected from 10, 30, 33, 46, 47, 50, 54, 63, 71, 74, 77, 82, 84, 88 or 90. Even more in particular, the mutant viruses are resistant towards the therapy the patient is taken.

A vector comprising an HIV sequence having at least one mutation in the HIV protease gene chosen from 41S, 41T, 41I, 41K, 41G and 70E may be useful for the phenotypic analysis. In particular, a vector comprising an HIV sequence having at least one mutation in the HIV protease gene chosen from 41T, 41I, 41K, 41G and 70E may be useful for the phenotypic analysis. The present knowledge about the correlation between a fold change in susceptibility and the presence of at least one mutation selected from 41S, 41T, 41I, 41K, 41G and 70E in HIV protease can be used to prepare an isolated and purified HIV protease sequence having at least one mutation selected from 41S, 41T, 41I, 41K, 41G and 70E. In particular, the knowledge about the correlation between a fold change in susceptibility and the presence of at least one mutation selected from 41T, 41I, 41K, 41G and 70E in HIV protease can be used to prepare an isolated and purified HIV protease sequence having at least one mutation selected from 41T, 41I, 41K, 41G and 70E.

The knowledge of the mutations of the present invention offers the possibility to develop probes and primers directed to said mutations. An isolated and purified oligonucleotide comprising a HIV protease sequence of 5 to 100 bases comprising at least one mutation chosen from 41S, 41T, 41I, 41K, 41G and 70E, may be useful for in vitro diagnosis of viral drug resistance. In particular, an isolated and purified oligonucleotide comprising a HIV protease sequence of 5 to 100 bases comprising at least one mutation chosen from 41T, 41I, 41K, 41G and 70E, may be useful for in vitro diagnosis of viral drug resistance. Suitable oligonucleotides for nucleic acid amplifying technologies contain 5 to 35 nucleic acid bases. Suitably such oligonucleotides contain 15 to 30 nucleic acid bases. An oligonucleotide may contain the mutant base at the 3' end so as to enable the detection of the mutant using PCR. Oligonucleotides may also be used as probes including molecular beacons (Tyagi, Nature Biotechnol 1998, 16(1) 49-53), and TaqMan probes.

A computer system comprising at least one database correlating the presence of at least one mutation in a human immunodeficiency virus protease and fold change in susceptibility of at least one strain of HIV to a protease inhibitor, comprising at least one record corresponding to a correlation between at least one mutation selected from 41S, 41T, 41I, 41K, 41G and 70E, in particular 41T, 41I, 41K, 41G and 70E, and treatment with at least a protease inhibitor can be used for evaluating resistance towards therapy.

A neural network that predicts the development of therapeutic agent resistance or sensitivity against at least one viral strain comprising at least one mutation selected from 41S, 41T, 41I, 41K, 41G and 70E can be used (WO 01/95230). In particular, a neural network that predicts the development of therapeutic agent resistance or sensitivity against at least one viral strain comprising at least one mutation selected from 41T, 41I, 41K, 41G and 70E can be used (WO 01/95230).

Genotyping Methodologies

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Assays for detection of mutations in HIV-1 may be based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., AIDS 5, 137-144 (1991); Richman, D. D., et al., J. Infect. Dis. 164, 1075-1081 (1991); Gingeras, T. R., et al., J. Infect. Dis. 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., J. Acq. Imm. Def. Syndr. Human Retrovirol. 9, 264-273 (1995); Holodniy, M., et al., J. Virol. 69, 3510-3516 (1995); Eastman, P. S., et al., J. Clin. Micro. 33, 2777-2780 (1995).); Line Probe Assay (LiPA® HIV-11 RT, Innogenetics) (Stuyver, L., et al., Antimicrob. Agents Chemotherap. 41, 284-291 (1997)); and biochip technology such as GENECHIP® technology (Affymetrix) (D'Aquila, R. T. Clin. Diagnost. Virol. 3, 299-316 (1995); Fodor, S. P. A. et al., Nature 364, 555-556 (1993); Fodor, S. P. A. Nature 227, 393-395 (1997). The sequence may also be determined using mass spectroscopic technologies. DNA sequencing assays provide information on all nucleotides of the sequenced region. Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance may be omitted.

Phenotyping Methodologies

Phenotyping assays measure the ability of a replicating virus to grow in the presence of compounds compared to a wild-type reference virus such as e.g. HIV-1/LAI, HIV-1/NL4.3, HIV-1/HXB2 or e.g. HIV-2/ROD. Alternatively, phenotyping assays are performed with pseudotyped viruses not able to replicate (WO 02/38792). Consequently, these assays directly measure the degree of viral susceptibility to specific inhibitors. In this case, one measures the effect of all mutational interactions, the effects of genetic changes as yet unknown or not previously identified, the effect of the background genotype, etc., on the phenotype. Some phenotypic assays are discussed below.

Cytopathic Effect Assay (CPE Assay)

Determination of the antiviral activity of a compound was done as described in Pauwels R. et al. (J Virol Methods 1988; 20(4):309-21). Various concentrations of the test compounds were brought into each well of a flat-bottom microtiter plate. Subsequently, HIV and MT4 cells were added to a final concentration of 200-250 50% cell culture infectious doses ($CCID_{50}$)/well and 30,000 cells/well, respectively. After 5 days of incubation (37° C., 5% $CO_2$), the cytopathic effect of the replicating virus was determined by the tetrazolium colorimetric MTT method. The dose protecting 50% of the cells from virus cytopathic effect was defined as the $EC_{50}$, while the dose achieving 90% protection was defined as the $EC_{90}$.

Reporter Gene Assay

The reporter gene assay used MT4-LTR-EGFP cells. Upon infection by HIV-1, the expression of the viral tat product increases transcription from the HIV-1 LTR promoter, leading to high-level expression of the reporter gene product. The assay procedure was similar to the CPE assay, except for the end reading of the assay, which was performed on day 3 by measuring the relative fluorescence of treated cultures and comparing this with the relative fluorescence of untreated cultures. The $EC_{50}$ or the $EC_{90}$ of a compound was defined as the concentration that inhibited the relative fluorescence by 50% or 90% respectively.

Antiviral Assay with PBMC Cultures

The purification and activation of PBMCs as well as the antiviral assays were carried out as described (CDER. Guidance for Industry Points to Consider in the Preclinical Development of Antiviral Drugs. 1990). The assay measured the extent that a drug inhibits HIV p24 antigen production by peripheral blood mononuclear cells (PBMC) cultures acutely infected with a viral strain. The susceptibility determination uses phytohaemaglutinine (PHA)-stimulated PBMCs from normal donors. In the in vitro infection experiments 1000 $CCID_{50}$ per million PHA-stimulated PBMCs was used. Cultures were split ½ every 3 to 4 days and compound was added together with the addition of new medium.

The p24 antigen production was measured using a commercial kit, according to the manufacturer protocol (NEN), at the moment that the p24 production of untreated infected cultures is maximal; i.e. between 7 and 11 days after infection.

The % p24 production was calculated by means of following equation:

$$\% \ p24 = 100 \times \frac{[p24]_{Sample} - [p24]_{Mock\_Control}}{[p24]_{HIV\_Control} - [p24]_{Mock\_Control}}$$

where $[p24]_{Sample}$ is the p24 concentration in an infected treated culture, $[p24]_{HIV\_Control}$ is the p24 concentration in an infected untreated culture and $[p24]_{Mock\_Control}$ is the p24 concentration in a mock-infected culture. The dose achieving 50% p24 production according to the above formula was defined as the $EC_{50}$, while the dose achieving 10% p24 production according to the above formula was defined as the $EC_{90}$.

Antiviral Assay with Monocytes/Macrophages

The assay measured the extent that a drug inhibits HIV p24 antigen production by primary monocytes/macrophages acutely infected with HIV-1/BaL (300 $CCID_{50}$/ml). The susceptibility determination used monocytes/macrophages isolated from PBMCs from normal donors by plastic adherence. Every 5 days cultures were fed with complete medium containing the appropriate compound concentrations. The p24 antigen production was measured at day 14 after virus challenge and $EC_{50}$ and $EC_{90}$ values were calculated.

Recombinant Virus Assays

A recombinant virus assay (RVA) starts with the amplification of viral target sequences by means of PCR. The amplicons are incorporated into a proviral laboratory clone deleted for the sequences, present in the amplicon. This generates a stock of recombinant viruses. The viruses are tested for their ability to grow in the presence of different concentrations of drugs. Results are obtained by calculating $EC_{50}$ values for each inhibitor and by reporting the results as $EC_{50}$ values, expressed in μM concentrations, or by computing the ratio of the $EC_{50}$ values found for the recombinant virus to the $EC_{50}$ values found for a wild type susceptible laboratory virus tested in parallel. In the latter case, resistance is expressed as "fold-resistance" (fold change in susceptibility, FC) compared to a wild-type susceptible HIV-1 strain.

The use of reporter gene systems for susceptibility testing allows the implementation of laboratory automation and standardization (Pauwels, et al., J. Virol. Methods 20, 309-321 (1988); Paulous, S., et al., International Workshop on HIV Drug Resistance, Treatment Strategies and Eradication, St. Petersburg, Fla., USA. Abstr. 46 (1997); and Deeks, S. G., et al., 2nd International Workshop on HIV Drug Resistance and Treatment Strategies, Lake Maggiore, Italy. Abstr. 53 (1998)).

The Antivirogram® assay (Virco) (WO 97/27480) is based on homologous recombination of patient derived HIV-1 gag/PR/RT sequences into a proviral HIV-1 clone correspondingly deleted for the gag/PR/RT sequences. A similar assay (Phenosense® ViroLogic, WO 97/27319) is based on enzymatic ligation of patient-derived PR/RT sequences into a correspondingly deleted proviral vector carrying an indicator gene, luciferase, inserted in the deleted HIV-1 envelope gene. Another assay was developed by Bioalliance (Phenoscript, WO 02/38792). The development of high throughput phenotyping and genotyping assays has allowed the establishment of a database containing the phenotypic resistance data and the genotypic sequences of over 30,000 clinical isolates.

Experimental Part

EXAMPLE 1

The Identification of Mutational Patterns in HIV-1 Protease and the Correlated Phenotypic Resistance Plasma samples from HIV-1-infected individuals from routine clinical practice were obtained and shipped to the laboratory on dry ice and stored at −70° C. until analysis. Viral RNA was extracted from 200 μL patient plasma using the QIAAMP® Viral RNA Extraction Kit (Qiagen, Hilden, Germany), according to the manufacturers instructions. cDNA encompassing part of the pol gene was produced using Expand™ reverse transcriptase (Boehringer Mannheim). A 2.2 kb fragment encoding the protease and RT regions were amplified from patient-derived viral RNA by nested polymerase chain reaction (PCR) using PCR primers and conditions as described. (Hertogs K., et al., Antimicrob. Agents Chemother. 42: 269-276 (1998), WO 01/81624). This genetic material was used in phenotyping and genotyping experiments.

Phenotypic analysis was performed using the recombinant virus assay (Antivirogram®)(WO 97/27480). MT-4 cells (Harada S., et al, Science 229: 563-566 (1985).) were co-transfected with pol gene PCR fragments and the protease-RT deleted HIV-1 molecular clone, pGEM3ΔPRT. This resulted in viable recombinant viruses containing protease/RT from the donor PCR fragment. After homologous recombination of amplicons into a PR-RT deleted proviral clone, the resulting recombinant viruses were harvested, titrated and used for in vitro susceptibility testing to antiretroviral drugs. The results of this analysis were expressed as fold change in susceptibility, reflecting the fold change in mean $EC_{50}$ (μM) of a particular drug when tested with patient-derived recombinant virus isolates, relative to the mean $EC_{50}$ (μM) of the same drug obtained when tested with a reference wild-type virus isolate (IIIB/LAI).

Genotyping was performed by an automated population-based full-sequence analysis, through a dideoxynucleotide-based approach, using the BigDye™ terminator kit (Applied Biosystems, Inc.) and resolved on an ABI 377 DNA sequencer.

The genotypes are reported as amino acid changes at positions along the protease gene compared to the wild-type (HXB2) reference sequence. Analysis by VirtualPhenotype™ interpretational software (WO 01/79540) allowed detection of mutational patterns in the database containing the genetic sequences of the clinical isolates and linkage with the corresponding resistance profiles of the same isolates.

EXAMPLE 2

Susceptibility Analysis of HIV-1 Variants Constructed by Site-Directed Mutagenesis Mutations in the protease or RT coding region were created by site-directed mutagenesis, using the QuikChange® Site-Directed Mutagenesis Kit (STRATAGENE®), of a wild-type HXB2-D EcoRl-Pstl restriction enzyme fragment, encompassing the HIV-1 pol gene and cloned into pGEM3 (Promega). All mutant clones were verified by DNA sequence analysis. PCR fragments were prepared from the mutated clones and the altered protease coding regions were transferred into HIV-1 HXB2-D by homologous recombination as described above. The susceptibility of these recombinant viruses to drugs was determined by the MT-4 cell CPE protection assay.

EXAMPLE 3

In Vitro Selection of Resistant Strains

MT4-LTR-EGFP cells were infected at a multiplicity of infection (MOI) of 0.01 to 0.001 $CCID_{50}$/cell in the presence of inhibitor. The starting concentration of the inhibitor was two to three times the $EC_{50}$, a suboptimal concentration. The cultures were sub-cultivated and scored microscopically on virus-induced fluorescence and cytopathicity every 3-4 days. The cultures were sub-cultivated in the presence of the same compound concentration until signs of virus replication were observed. The escaping virus was further cultivated in the presence of the same inhibitor concentration in order to enrich the population in resistant variants. If full virus breakthrough was observed the supernatant was collected and stored (new virus strain). Afterwards, the same virus was challenged with a higher compound concentration in order to select variants able to grow in the presence of as high as possible inhibitor concentrations. From the new viruses, a virus stock was grown in the absence of inhibitor.

In vitro drug selection experiments starting from wild-type HIV-1 under pressure of compound 1, compound 2, and Nelfinavir (NFV) have been performed. Tables 1, 2, 3, 4, and 5 show the genotypic and phenotypic characterization of the selected strains.

TABLE 1

Characterization of the strains isolated from HIV-1/LAI in the presence of compound 1

| In vitro selection Experimental conditions | | | | |
|---|---|---|---|---|
| Starting strain | HIV/LAI | HIV-1/LAI | HIV-1/LAI | HIV-1/LAI |
| Compound | — | Compound 1 | Compound 1 | Compound 1 |
| Concentration (nM) | — | 30 | 100 | 100 |
| Days | — | 45 | 97 | 188 |

| Protease Genotype | | | | |
|---|---|---|---|---|
| Mutations | — | R41T | R41T K70E | R41T K70E |

Phenotype In vitro susceptibility to PIs N, median EC50 (nM), median FC

| | | | | | |
|---|---|---|---|---|---|
| Compound 1 | N | 37 | 7 | 6 | 3 |
| | EC50 | 3.2 | 7.7 | 26 | 44 |
| | FC | 1 | 2 | 8 | 10 |
| Indinavir | N | 16 | 3 | 3 | 2 |
| | EC50 | 28 | 33 | 98 | 140 |
| | FC | 1 | 1 | 4 | 5 |
| Ritonavir | N | 16 | 3 | 3 | 2 |
| | EC50 | 31 | 32 | 21 | 46 |
| | FC | 1 | 1 | 1 | 1 |
| Nelfinavir | N | 11 | 3 | 4 | 2 |
| | EC50 | 30 | 32 | 18 | 37 |
| | FC | 1 | 1 | 1 | 1 |
| Saquinavir | N | 46 | 2 | 6 | 3 |
| | EC50 | 7.8 | 30 | 35 | 150 |
| | FC | 1 | 4 | 4 | 20 |
| Amprenavir | N | 67 | 3 | 6 | 3 |
| | EC50 | 36 | 38 | 29 | 39 |
| | FC | 1 | 1 | 1 | 1 |
| Lopinavir | N | 11 | 3 | 5 | 3 |
| | EC50 | 7.9 | 27 | 32 | 47 |
| | FC | 1 | 3 | 4 | 6 |

TABLE 2

Characterization of the strains isolated from HIV-1/LAI in the presence of compound 1

| In vitro selection Experimental conditions | | | | | |
|---|---|---|---|---|---|
| Starting strain | HIV-1/LAI | HIV-1/LAI | HIV-1/LAI | HIV-1/LAI | HIV-1/LAI |
| Compound | — | Comp 1 | Comp 1 | Comp 1 | Comp 1 |
| Concentration (nM) | — | 30 | 100 | 100 | 200 |
| Days | — | 70 | 139 | 195 | 328 |

TABLE 2-continued

Characterization of the strains isolated from HIV-1/LAI in the presence of compound 1

| Protease Genotype | | | | | |
|---|---|---|---|---|---|
| Mutations | — | K70E | S37S/N R41R/K K70E | S37N R41S K70E | S37N R41S K70E |

Phenotype In vitro susceptibility to PIs N, median EC50 (nM), median FC

| | | | | | | |
|---|---|---|---|---|---|---|
| Compound 1 | N | 5 | 1 | 1 | 1 | 1 |
| | EC50 | 2.6 | 6.5 | 2.5 | 4.7 | 0.4 |
| | FC | 1 | 3 | 1 | 2 | 0.2 |
| IDV | N | 4 | 1 | 1 | 2 | 1 |
| | EC50 | 12 | 18 | 6.3 | 9.1 | 5.5 |
| | FC | 1 | 2 | 1 | 1 | 0.5 |
| RTV | N | 3 | 1 | 1 | 2 | 1 |
| | EC50 | 33 | 47 | 22 | 14 | 31 |
| | FC | 1 | 1 | 1 | 0.4 | 1 |
| NFV | N | 4 | 1 | 1 | 2 | 1 |
| | EC50 | 38 | 39 | 9.7 | 9.5 | 1.9 |
| | FC | 1 | 1 | 0.3 | 0.3 | 0.1 |
| SQV | N | 3 | 1 | 1 | 1 | 1 |
| | EC50 | 5.6 | 6.0 | 0.7 | 0.9 | 4.0 |
| | FC | 1 | 1 | 0.1 | 0.2 | 1 |
| APV | N | 5 | 1 | 1 | 2 | 1 |
| | EC50 | 20 | 56 | 24 | 14 | 15 |
| | FC | 1 | 3 | 1 | 1 | 1 |
| LPV | N | 5 | 1 | 1 | 2 | 1 |
| | EC50 | 4.6 | 17 | 2.8 | 3.9 | 1.1 |
| | FC | 1 | 4 | 1 | 1 | 0.2 |

TABLE 3

Characterization of the strains isolated from HIV-1/LAI in the presence of compound 2

| In vitro selection Experimental conditions | | | | |
|---|---|---|---|---|
| Starting strain | HIV-1/LAI | HIV-1/LAI | HIV-1/LAI | HIV-1/LAI |
| Compound | — | Compound 2 | Compound 2 | Compound 2 |
| Concentration (nM) | — | 100 | 100 | 100 |
| Days | — | 116 | 200 | 264 |

| Protease Genotype | | | | |
|---|---|---|---|---|
| Mutations | — | R41I | G16G/H R41I | G16E R41I |

Phenotype In vitro susceptibility to PIs N, median EC$_{50}$ (nM), median FC

| | | | | | |
|---|---|---|---|---|---|
| Compound 2 | N | 2 | | 2 | 1 |
| | EC50 | 12 | | 6.9 | 61 |
| | FC | 1 | | 1 | 5 |
| IDV | N | 4 | | 1 | 1 |
| | EC50 | 12 | | 19 | 47 |
| | FC | 1 | | 2 | 4 |
| RTV | N | 3 | | 2 | 1 |
| | EC50 | 33 | | 22 | 23 |
| | FC | 1 | | 1 | 1 |

TABLE 3-continued

Characterization of the strains isolated from HIV-1/LAI in the presence of compound 2

| | | | | | |
|---|---|---|---|---|---|
| NFV | N | 4 | | 2 | 1 |
| | EC50 | 38 | | 16 | 14 |
| | FC | 1 | | 0 | 0 |
| SQV | N | 3 | | | 1 |
| | EC50 | 5.6 | | | 45 |
| | FC | 1 | | | 8 |
| APV | N | 5 | | 2 | 1 |
| | EC50 | 20 | | 14 | 8.4 |
| | FC | 1 | | 1 | 0 |
| LPV | N | 5 | | 2 | 1 |
| | EC50 | 4.6 | | <0.9 | 18 |
| | FC | 1 | | 0 | 4 |

TABLE 4

Characterization of the strains isolated from HIV-1/LAI in the presence of compound 1

In vitro selection
Experimental conditions

| Starting strain | HIV-1/LAI | HIV-1 | HIV-1 | HIV-1 | HIV-1 |
|---|---|---|---|---|---|
| Compound | — | — | Comp 1 | Comp 1 | Comp 1 |
| Concentration (nM) | — | — | 20 | 40 | 40 |
| Days | — | — | 94 | 161 | 175 |

Protease Genotype

| Mutations | — | — | R41G/R V82V/I | R41G V82I | R41G V82I |
|---|---|---|---|---|---|

Phenotype
In vitro susceptibility to PIs
N, median $EC_{50}$ (nM), median FC

| Compound 1 | N | 5 | 1 | 1 | 1 | 1 |
|---|---|---|---|---|---|---|
| | EC50 | 2.6 | 3.4 | 1.1 | 2.6 | 1.9 |
| | FC | 1 | 1 | 0 | 1 | 1 |
| IDV | N | 4 | 1 | 1 | 1 | 1 |
| | EC50 | 12 | 2.4 | 3.1 | 2.1 | 3.9 |
| | FC | 1 | 0 | 0 | 0 | 0 |
| RTV | N | 3 | 1 | 1 | 1 | 1 |
| | EC50 | 33 | 22 | 4.2 | 6.3 | 1.7 |
| | FC | 1 | 1 | 0 | 0 | 0 |
| NFV | N | 4 | 1 | 1 | 1 | 1 |
| | EC50 | 38 | 31 | 5.7 | 11 | 16 |
| | FC | 1 | 1 | 0 | 0 | 0 |
| SQV | N | 3 | 1 | 1 | 1 | 1 |
| | EC50 | 5.6 | 8.9 | 0.9 | 1.0 | 0.8 |
| | FC | 1 | 2 | 0 | 0 | 0 |
| APV | N | 5 | 1 | 1 | 1 | 1 |
| | EC50 | 20 | 26 | 7.3 | 6.6 | 9.4 |
| | FC | 1 | 1 | 0 | 0 | 0 |
| LPV | N | 5 | 1 | 1 | 1 | 1 |
| | EC50 | 4.6 | 6.8 | 2.0 | 1.8 | 1.0 |
| | FC | 1 | 1 | 0 | 0 | 0 |

TABLE 5

Characterization of the strains isolated from HIV-1/LAI in the presence of nelfinavir (NFV)

In vitro selection
Experimental conditions

| Starting strain | HIV-1/LAI | HIV-1/LAI | HIV-1/LAI | HIV-1/LAI | HIV-1/LAI |
|---|---|---|---|---|---|
| Compound Concentration (nM) | — | NFV 1000 | NFV 3000 | NFV 9000 | NFV 9000 |
| Days | — | 35 | 69 | 111 | 140 |

Protease Genotype

| Mutations | — | D30N | L10F D30N M46I V77I I85V/I N88D/N | L10F D30N R41R/K K45I/K M46I V77I I84V/I I85V/I N88D | L10F D30N R41R/K K45I/K M46I V77I I84V N88D |
|---|---|---|---|---|---|

Phenotype
In vitro susceptibility to PIs
N, median $EC_{50}$ (nM), median FC

| IDV | N | 4 | 1 | | 1 | 1 |
|---|---|---|---|---|---|---|
| | EC50 | 12 | 7.9 | | 100 | 28 |
| | FC | 1 | 1 | | 8 | 2 |
| RTV | N | 3 | 1 | 1 | 1 | 1 |
| | EC50 | 33 | 19 | 27 | 86 | 170 |
| | FC | 1 | 1 | 1 | 3 | 5 |
| NFV | N | 4 | 1 | | 1 | 1 |
| | EC50 | 38 | 330 | | 7200 | 6800 |
| | FC | 1 | 9 | | 200 | 200 |
| SQV | N | 3 | 1 | 1 | 1 | 1 |
| | EC50 | 5.6 | 1.8 | 2.5 | 15 | 34 |
| | FC | 1 | 0 | 0 | 3 | 6 |
| APV | N | 5 | 1 | 1 | 1 | 1 |
| | EC50 | 20 | 28 | 59 | 95 | 190 |
| | FC | 1 | 1 | 3 | 5 | 10 |
| LPV | N | 5 | 1 | 1 | 1 | 1 |
| | EC50 | 4.6 | 7.7 | 24 | 39 | 56 |
| | FC | 1 | 2 | 5 | 8 | 10 |

The in vitro antiviral activity of compound 1, compound 2, Nelfinavir, and current PIs against the selected strains was evaluated in acutely infected MT4 cells. Median $EC_{50}$ values together with the number of determinations (N), and the fold change in $EC_{50}$ as compared to wild type (FC) are reported.

The invention claimed is:

1. A method for evaluating the effectiveness of a protease inhibitor as an antiviral therapy for a patient infected with at least one mutant HIV strain comprising:
    (i) collecting a sample from an HIV-infected patient;
    (ii) extracting the nucleic acid from said patient sample;
    (iii) determining the amino acid sequence encoded by said nucleic acid;
    (iv) determining whether said amino acid sequence comprises at least one mutation selected from R41S, R41T, R41I, R41G and K70E in the protease region;
    (v) measuring the effectiveness of said protease inhibitor against said mutant HIV strain;
    (vi) correlating the presence of said at least one mutation of step (iv) to a change in the effectiveness of said protease inhibitor against said mutant HIV strain relative to the effectiveness of said protease inhibitor against a wild type HIV strain (HIV IIIB/LAI reference sequence).

2. A method for evaluating the effectiveness of a protease inhibitor as an antiviral therapy for a patient infected with at least one mutant HIV strain comprising:

(i) collecting a sample from an HIV-infected patient;
(ii) extracting the nucleic acid from said patient sample;
(iii) determining the amino acid sequence encoded by said nucleic acid;
(iv) determining whether said amino acid sequence comprises at least one mutation selected from R41T, R41I, R41G and K70E in the protease region;
(v) measuring the effectiveness of said protease inhibitor against said mutant HIV strain;
(vi) correlating the presence of said at least one mutation of step (iv) to a change in the effectiveness of said protease inhibitor for said patient relative to the effectiveness of said protease inhibitor for a patient infected with a wild type HIV strain (HIV IIIB/LAI reference sequence).

3. A method for evaluating a change in the susceptibility of a HIV strain to a protease inhibitor comprising the steps of:
(i) collecting a sample from an HIV-infected patient;
(ii) extracting the nucleic acid from said patient sample;
(iii) determining the amino acid sequence encoded by said nucleic acid;
(iv) determining whether said amino acid sequence comprises at least one mutation selected from R41S, R41T, R41G and K70E in the protease region;
(v) measuring the susceptibility of said HIV strain from said patient to said protease inhibitor;
(vi) correlating the presence of said at least one mutation of step (iv) to a change in susceptibility of the patient HIV strain to said protease inhibitor relative to the susceptibility of a wild type HIV strain (HIV IIIB/LAI reference sequence) to said protease inhibitor.

4. A method for evaluating a change in the susceptibility of a HIV strain to a protease inhibitor comprising the steps of:
(i) collecting a sample from an HIV-infected patient;
(ii) extracting the nucleic acid from said patient sample;
(iii) determining the amino acid sequence encoded by said nucleic acid;
(iv) determining whether said amino acid sequence comprises at least one mutation selected from R41T, R41G and K70E in the protease region;
(v) measuring the susceptibility of said HIV strain from said patient to said protease inhibitor;
(vi) correlating the presence of said at least one mutation of step (iv) to a change in susceptibility of the patient HIV strain to said protease inhibitor relative to the susceptibility of a wild type HIV strain (HIV IIIB/LAI reference sequence) to said protease inhibitor.

* * * * *